United States Patent [19]

Rohrmann et al.

[11] Patent Number: 5,733,991
[45] Date of Patent: Mar. 31, 1998

[54] PROCESS FOR PREPARING CYCLOOLEFIN POLYMER

[75] Inventors: Jürgen Rohrmann, Kelkheim; Michael-Joachim Brekner, Frankfurt am Main; Frank Küber, Oberursel; Frank Osan, Kelkheim; Thomas Weller, Mainz, all of Germany

[73] Assignee: Hoechst Aktiengesellschaft, Germany

[21] Appl. No.: 730,739

[22] Filed: Oct. 15, 1996

Related U.S. Application Data

[63] Continuation of Ser. No. 420,449, Apr. 10, 1995, abandoned, which is a continuation of Ser. No. 195,559, Feb. 14, 1994, abandoned.

[30] Foreign Application Priority Data

Feb. 12, 1993 [DE] Germany ............ 43 04 293.7

[51] Int. Cl.$^6$ .................. C08F 4/64; C08F 32/04; C08F 4/62
[52] U.S. Cl. .................. 526/160; 502/103; 502/104; 502/117; 502/232; 502/242; 526/126; 526/127; 526/160; 526/281; 526/308; 526/348; 526/348.2; 526/348.3
[58] Field of Search .................. 502/103, 232, 502/242

[56] References Cited

U.S. PATENT DOCUMENTS

| 4,892,851 | 1/1990 | Ewen ............ 502/104 |
| 5,087,677 | 2/1992 | Brekner et al. ............ 502/104 |

FOREIGN PATENT DOCUMENTS

| 11465/92 | 9/1992 | Australia. |
| 2055397 | 5/1992 | Canada. |
| 0 407 870 | 1/1991 | European Pat. Off.. |
| 0 485 893 | 5/1992 | European Pat. Off.. |
| 0 503 422 | 9/1992 | European Pat. Off.. |

*Primary Examiner*—Fred Zitomer
*Attorney, Agent, or Firm*—Connolly & Hutz

[57] ABSTRACT

Cycloolefin polymers having a high viscosity number are obtained by polymerization of a polycyclic olefin and, if desired, an acyclic olefin and/or a monocyclic olefin in the presence of a catalyst system which comprises an aluminoxane and a metallocene compound of the formula

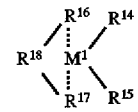

in which $R^{16}$ is fluorenyl or indenyl and $R^{17}$ is cyclopentadienyl and the bridge $R^{18}$ contains silicon.

17 Claims, No Drawings

PROCESS FOR PREPARING CYCLOOLEFIN POLYMER

Continuation of Ser. No. 08/420,449, Apr. 10, 1995, abandoned, which is a Continuation of Ser. No. 08/195,559, Feb. 14, 1995, abandoned.

The invention relates to a process for preparing homopolymers and copolymers of polycyclic olefins having high viscosity numbers.

Metallocene/aluminoxane catalyst systems can be used to prepare cycloolefin homopolymers and copolymers. The polymerization of the cycloolefins proceeds in bulk or in solvents in the presence of metallocene catalysts with retention of the rings (EP 407870, EP 485893). The solvents used are mainly hydrocarbons.

Cycloolefin copolymers having a high cycloolefin content and also cycloolefin homopolymers, because of their high glass transition temperature, possess high thermal shape stability and are therefore important materials which are used as thermoplastic molding compounds. The mechanical properties are thus mainly determined by the ratio of the incorporated comonomers, which is characterized by the glass transition temperature. In addition, depending on the application, different melt viscosities of the polymer are required. Thus, injection molding applications require relatively low melt viscosities, while extrusion applications, deep drawing or certain film applications require high melt viscosities so as to ensure sufficient tenacity of the polymer melt during processing.

For a given processing temperature and comonomer composition, the melt viscosity of cycloolefin copolymers increases with the average molecular weight and thus with the viscosity number VN.

The viscosity number of cycloolefin polymers is, according to the prior art, mainly controlled by metering in of hydrogen and, as far as technically possible, by variation of the polymerization temperature.

To reduce the viscosity number, either hydrogen regulation can be used or the polymerization temperature can be increased. On the other hand, the viscosity number can be increased only by lowering the temperature. There are, however, technical limits placed on the extent to which the temperature can be lowered, since at low polymerization temperatures a constant temperature over time is no longer ensured. This can be attributed to the efficiency of cooling increasing with the temperature difference between polymerization and cooling temperatures. Since, for economic reasons, cooling is carried out with river water, a polymerization process which proceeds below 35° C. can no longer be cooled economically. In addition, at low polymerization temperatures the activity of the catalyst system and thus the reaction rate are reduced too far. The hitherto known processes can be used to prepare primarily injection-molding cycloolefin polymers which have a relatively low melt viscosity.

It is an object of the invention to find a process which makes it possible to obtain cycloolefin polymers which, for a given glass transition temperature and predetermined polymerization temperature, particularly at industrially important temperatures (above 35° C.), have a high viscosity number.

It has been found that this object can be achieved with the use of specific metallocene catalysts. It has furthermore been found that the use of catalyst mixtures which contain the specific metallocene catalysts makes it possible to prepare polymers having a bimodal or multimodal molecular weight distribution. The polymerization is carried out in the liquid cycloolefin itself or in cycloolefin solution, with the pressure advantageously lying above 1 bar.

The invention provides a process for preparing a cycloolefin homopolymer or copolymer by polymerization of from 0.1 to 100% by weight, based on the total amount of monomers, of at least one polycyclic olefin of the formulae I, II, III, IV, V or VI

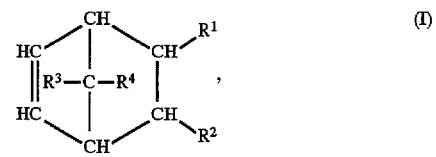

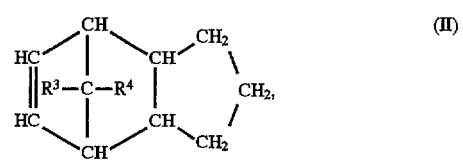

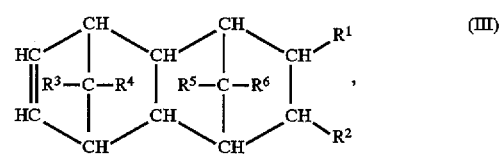

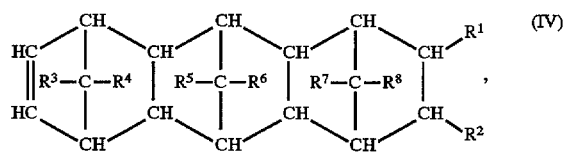

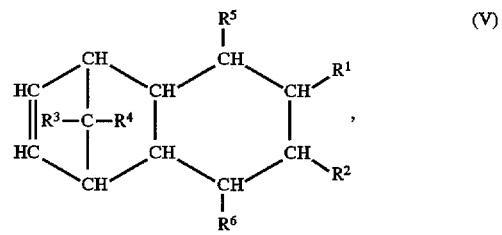

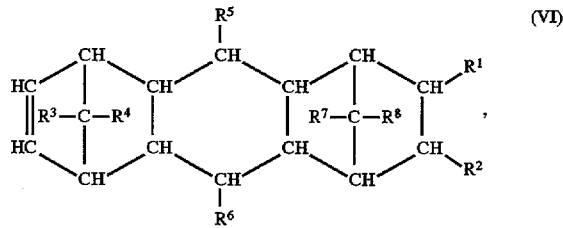

in which $R^1$, $R^2$, $R^3$, $R^4$, $R^5$, $R^6$, $R^7$ and $R^8$ are identical or different and are a hydrogen atom or a hydrocarbon radical, with the same radicals in the various formulae being able to have a different meaning, from 0 to 99.9% by weight, based on the total amount of monomers, of a cycloolefin of the formula VII

in which n is a number from 2 to 10, and from 0 to 99.9% by weight, based on the total amount of monomers, of at least one acyclic 1-olefin of the formula VIII

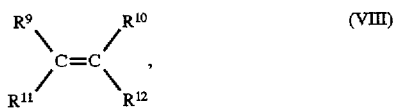

in which $R^9$, $R^{10}$, $R^{11}$ and $R^{12}$ are identical or different and are a hydrogen atom or a hydrocarbon radical, at a temperature from $-78°$ to $150°$ C. and a pressure from 0.01 to 64 bar, in the presence of a catalyst which comprises an aluminoxane of the formula IX

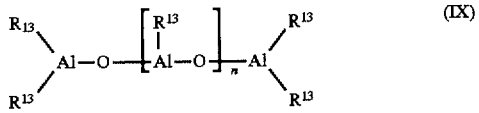

for the linear type and/or of the formula X

for the cyclic type, with, in the formulae IX and X, $R^{13}$ being a $C_1$–$C_6$-alkyl group or phenyl or benzyl and n being an integer from 2 to 50, and a metallocene of the formula XI

in which $M^1$ is titanium, zirconium, hafnium, vanadium, niobium or tantalum, $R^{14}$ and $R^{15}$ are identical or different and are a hydrogen atom, a halogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group or a $C_8$–$C_{40}$-arylalkenyl group, $R^{16}$ is a fluorenyl group or an indenyl group and $R^{17}$ is a cyclopentadienyl group, wherein $R^{18}$ is

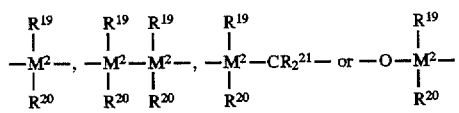

in which $M^2$ is silicon and $R^{19}$, $R^{20}$ and $R^{21}$ are identical or different and are a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{19}$ and $R^{20}$ or $R^{19}$ and $R^{21}$ in each case form a ring with the atoms connecting them.

In the process of the invention, at least one polycyclic olefin of the formula I, II, III, IV, V or VI is polymerized, preferably a cycloolefin of the formula I or III, in which $R^1$, $R^2$, $R^3$, $R^4$, $R^5$, $R^6$, $R^7$ and $R^8$ are identical or different and are a hydrogen atom or a hydrocarbon radical, preferably a $C_6$–$C_{10}$-aryl radical or a $C_1$–$C_8$-alkyl radical, with the same radicals in the various formulae being able to have a different meaning.

If desired, a monocyclic olefin of the formula VII

in which n is a number from 2 to 10, is also used. Another comonomer is an acyclic 1-olefin of the formula VIII,

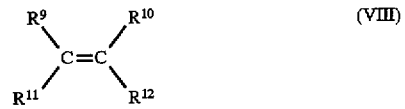

in which $R^9$, $R^{10}$, $R^{11}$ and $R^{12}$ are identical or different and are a hydrogen atom or a $C_1$–$C_8$-alkyl radical. Preference is given to ethylene and propylene.

In particular, copolymers of polycyclic olefins, preferably of the formulae I and III, with the acyclic olefins of the formula VIII are prepared.

Particularly preferred cycloolefins are norbornene and tetracyclododecene, with these able to be substituted by $(C_1$–$C_6)$-alkyl. They are preferably copolymerized with ethylene; ethylene/norbornene copolymers are of particular importance.

The polycyclic olefin of the formula I, II, III, IV, V or VI is used in an amount from 0.1 to 100% by weight and the monocyclic olefin of the formula VII is used in an amount from 0 to 99.9% by weight, in each case based on the total amount of monomers.

The concentration of the acyclic olefin of the formula VIII is determined by the solubility of the open-chain olefin in the reaction medium at the given pressure and given temperature.

Polycyclic olefins, monocyclic olefins and acyclic olefins are taken to also include mixtures of two or more olefins of the respective type. This means that terco-polymers and multicopolymers can also, besides the polycyclic homopolymers and bicopolymers, be prepared by the process of the invention. In addition, copolymers of the cycloolefins of the formula VII with the acyclic olefins of the formula VIII can be advantageously prepared by the process described.

Of the cycloolefins of the formula VII, preference is given to cyclopentene, which may be substituted.

The catalyst to be used for the process of the invention comprises an aluminoxane and at least one metallocene (transition metal component) of the formula XI

In the formula XI, $M^1$ is a metal selected from the group comprising titanium, zirconium, hafnium, vanadium, niobium and tantalum, preferably zirconium and hafnium. Particular preference is given to using zirconium.

$R^{14}$ and $R^{15}$ are identical or different and are a hydrogen atom, a $C_1$–$C_{10}$-, preferably $C_1$–$C_3$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{12}$-alkylaryl group, a $C_8$–$C_{10}$-, preferably $C_8$–$C_{12}$-arylalkenyl group or a halogen atom, preferably chlorine.

$R^{16}$ is a fluorenyl group or an indenyl group, preferably a 2,7-dialkylfluorenyl group, and $R^{17}$ is a cyclopentadienyl group. If desired, one or both radicals $R^{16}$ and $R^{17}$ can also bear one or more radicals $R^{22}$ which are identical or different and are a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkyl-aryl group. Particular preference is given to $R^{16}$ being a 2,7-di-tert-butylfluorenyl group.

$R^{18}$ is a single-membered or multi-membered bridge which links the radicals $R^{16}$ and $R^{17}$ and is

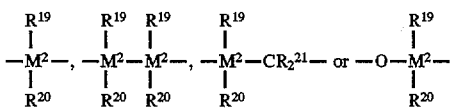

in which $M^2$ is silicon and $R^{19}$, $R^{20}$ and $R^{21}$ are identical or different and are a hydrogen atom, a halogen atom, a $C_1$–$C_{10}$-alkyl group, preferably a $C_1$–$C_4$-alkyl group, particularly preferably a methyl group, a $C_1$–$C_{10}$-fluoroalkyl group, a $C_6$–$C_{10}$-aryl group, preferably a phenyl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{19}$ and $R^{20}$ or $R^{19}$ and $R^{21}$ in each case form a ring with the atoms connecting them.

Preferably $R^{18}$ is a radical

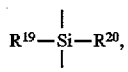

particular preference is given to

Preference is given to using the metallocenes:
dimethylsilandiyl(9-fluorenyl)cyclopentadienylzirconium dichloride,
dimethylsilandiyl(9-(2,7-di-tert-butyl)fluorenyl) cyclopentadienylzirconium dichloride,
1-silacyclobutyl(9-fluorenyl)cyclopentadienylzirconium dichloride,
dibenzylsilandiyl(9-fluorenyl)cyclopentadienylzirconium dichloride or mixtures of at least two of these catalysts. A particularly suitable metallocene is:
dimethylsilandiyl(9-(2,7-di-tert-butyl)fluorenyl) cyclopentadienylzirconium dichloride.

The substitution of the fluorene is carried out by synthetic steps known from the literature (Liebigs Ann. 1976, page 74; Synthesis 1984, page 335, to which explicit reference is made herewith); furthermore, the bridged metallocenes are prepared, for example, according to the reaction schemes known from EP 485893.

The aluminoxane preferably has the formula IX and/or the formula X. In these formulae, the radicals $R^{13}$ can be identical or different and are a $C_1$–$C_6$-alkyl group, preferably methyl, ethyl or isobutyl, butyl or neopentyl, or phenyl or benzyl. Particular preference is given to methyl. n is an integer from 0 to 50, preferably from 5 to 40.

The aluminoxane can be prepared in various ways according to known processes. One method is, for example, reacting an aluminum-hydrocarbon compound and/or a hydrido-aluminum-hydrocarbon compound with water (gaseous, solid, liquid or bound, for example as water of crystallization) in an inert solvent (such as toluene). For the preparation of an aluminoxane having different alkyl groups $R^{13}$, two different aluminum trialkyls ($AlR_3$+$AlR'_3$) corresponding to the desired composition are reacted with water (cf. S. Pasynkiewicz, Polyhedron 9 (1990) 429 and EP-A 302 424, to which explicit reference is made herewith).

The exact steric structure of the aluminoxanes is not known.

Regardless of the manner of preparation, all aluminoxane solutions have in common a changing content of unreacted aluminum starting compound which is present in free form or as an adduct.

It is also possible to apply the aluminoxane to a support and then to use it as a suspension in supported form. A number of supporting processes are known (EP 92107331.8); for example silica gel can function as the support.

It is possible to preactivate the metallocene with an aluminoxane of the formula IX and/or X prior to use in the polymerization. The polymerization activity is thereby significantly increased.

The preactivation of the transition metal compound is carried out in solution. Preferably, the metallocene is dissolved in a solution of the aluminoxane in an inert hydrocarbon. A suitable inert hydrocarbon is an aliphatic or aromatic hydrocarbon. Preference is given to using toluene.

The concentration of the aluminoxane in the solution lies in the range from about 1% by weight to the saturation limit, preferably from 5 to 30% by weight, in each case based on the total solution. The metallocene can be used in the same concentration, but preferably it is used in an amount of $10^{-4}$–1 mol per mole of aluminoxane. The preactivation time is from 5 minutes to 60 hours, preferably from 5 to 60 minutes. The reaction is carried out at a temperature from $-78°$ C. to $150°$ C., preferably from $0°$ to $70°$ C.

The metallocene is preferably used in the form of the racemate. It can also be prepolymerized or applied to a support. For prepolymerization, the (or one of the) olefin(s) used in the polymerization is preferably employed.

Suitable supports are, for example, silica gels, aluminum oxides, solid aluminoxane or other inorganic support materials. Another suitable support material is a polyolefin powder in finely divided form.

A further possible embodiment of the process of the invention comprises using, in place of or in addition to an aluminoxane, a salt-like compound of the formula $R_xNH_{4-x}BR'_4$ or of the formula $R_3PHBR'_4$ as co-catalyst. Here, $x=1$, 2 or 3, R=alkyl or aryl, identical or different, and R'=aryl which may also be fluorinated or partially fluorinated. In this case the catalyst comprises the reaction product of a metallocene with one of the specified compounds (EP 277 004).

If solvent is added to the reaction mixture, then it is a customary inert solvent such as, for example, an aliphatic or cycloaliphatic hydrocarbon, petroleum fractions or hydrogenated diesel oil fractions or toluene.

The metallocene compound is used in a concentration, based on the transition metal, from $10^{-3}$ to $10^{-8}$, preferably from $10^{-4}$ to $10^{-7}$, mol of transition metal per dm$^3$ of reactor volume. The aluminoxane is used in a concentration from $10^{-4}$ to $10^{-1}$, preferably from $10^{-4}$ to $2\times10^{-2}$, mol per dm$^3$ of reactor volume, based on the aluminum content. However, higher concentrations are also possible in principle.

In the preparation of copolymers, the molar ratios of the polycyclic olefin to the open-chain olefin used can vary over a wide range. Preferably, molar ratios from 3:1 to 100:1 of cycloolefin to open-chain olefin are used. Selection of the polymerization temperature, the concentration of the catalyst components and the molar ratio used or the pressure of the gaseous, open-chain olefin allow the incorporated amount of comonomer to be controlled to almost any value desired. Preference is given to the incorporation of between 20 and 80 mol % of the cyclic components and particular preference is given to the incorporation of between 40 and 60 mol % of the cyclic components.

The polymerization can also be carried out in a number of stages, by means of which block copolymers can also be formed (P 42 05 416.8).

The average molecular weight of the polymer formed can furthermore be controlled in a known manner by metering in of hydrogen or variation of the temperature.

If the opportunities offered by lowering the molecular weight by hydrogen regulation are considered, then the process of the invention significantly broadens the accessible molecular weight range of extrudable cycloolefin copolymers.

The polymerization is preferably carried out at temperatures from 35° to 100° C., particularly preferably at temperatures from 60° to 80° C. The cycloolefin copolymers prepared according to the invention have viscosity numbers in the range from 150 to 600 cm$^3$/g, preferably from 170 to 500 cm$^3$/g and glass transition temperatures in the range from 80° to 250° C., preferably from 125° to 220° C., particularly preferably from 140° to 190° C. They are particularly suitable for producing extruded parts such as films, hoses, pipes, rods and fibers. A further property of the materials prepared according to the invention is their transparency. This is of particular importance for the optical applications of the extruded parts made of these materials. The refractive index determined with an Abbe refractometer and mixed light of the reaction products described in the following examples lies in the range between 1.520 and 1.555. Since the refractive index lies very close to that of crown glass (n=1.51), the products of the invention can be used as a glass substitute in various applications such as, for example, lenses, prisms, support plates and films for optical data storage, as covering and focusing sheets for solar cells, as covering and dispersing disks for power optics, as optical waveguides in the form of fibers or films.

In impact-modified form, the materials of the invention can be used as a structural material in various industrial areas (P 42 13 219.3).

The cycloolefin polymers prepared according to the process of the invention can also be used for the preparation of polymer alloys. The alloys can be prepared in the melt or in solution. The alloys each have a favorable property combination of the components for certain applications. For alloys with the polymers of the invention, the following polymers can be used:

polyethylene, polypropylene, ethylene/propylene copolymers, polybutylene, poly(4-methyl-1-pentene), polyisoprene, polyisobutylene, natural rubber, poly(methyl methacrylate), further polymethacrylates, polyacrylates, acrylate/methacrylate copolymers, polystyrene, styrene/acrylonitrile copolymers, bisphenol-A polycarbonate, other polycarbonates, aromatic polyester carbonates, polyethylene terephthalate, polybutylene terephthalate, amorphous polyarylates, nylon-6, nylon-66, other polyamides, polyaramides, polyether ketones, polyoxymethylene, polyoxyethylene, polyurethanes, polysulfones, polyether sulfones, polyvinylidene fluoride.

The glass transition temperatures Tg given in the following examples were determined by DSC (Differential Scanning Calorimetry) at a heating rate of 20° C./min. The viscosity numbers given were determined in accordance with DIN 53 728.

Example 1

A 1.5 dm$^3$ reactor was charged with ethylene and 600 cm$^3$ of an 85 percent strength by weight solution of norbornene in toluene were introduced. By multiple pressurization with ethylene (6 bar), the solution was saturated with ethylene. The pressure was set to 6.0 bar (gage pressure), 5 cm$^3$ of methylaluminoxane solution in toluene (10.1% by weight of methylaluminoxane having a cryoscopically determined molecular weight of 1300 g/mol) were introduced into the reactor and the mixture was stirred at 70° C. for 15 minutes. A solution of 0.1 mg of dimethylsilyl(9-(2,7-di-tert-butyl)fluorenyl)cyclopentadienyl)zirconium dichloride in 5 cm$^3$ of methylaluminoxane solution in toluene was added after 15 minutes preactivation.

Polymerization was carried out at 70° C. for one hour while stirring (750 rpm), with the ethylene pressure being maintained at 6.0 bar by metering in further amounts.

The reaction solution was drained into a vessel and quickly introduced into 5 dm$^3$ of acetone, the mixture was stirred for 10 minutes and the precipitated product was subsequently filtered off. The filter cake was washed a number of times alternately with 10% strength hydrochloric acid and acetone. Finally the cake was washed to neutrality and stirred with acetone. The polymer thus washed is filtered off and dried at 80° C. and a pressure of 0.2 bar for 15 hours.

13 g of a colorless polymer were obtained. A viscosity number VN of 259 cm$^3$/g and a glass transition temperature Tg of 142° C. were measured on the polymer.

Examples 2, 3, 4 and 5

Polymerization was carried out as in Example 1, with the catalyst or the polymerization conditions being varied as shown in Table 1.

Example 6 (Comparative Example for Example 1)

A 1.5 dm$^3$ reactor was charged with ethylene and 600 cm$^3$ of an 85 percent strength by weight solution of norbornene in toluene were introduced. By multiple pressurization with ethylene (6 bar), the solution was saturated with ethylene. The pressure was set to 6.0 bar (gage pressure), 5 cm$^3$ of methylaluminoxane solution in toluene (10.1% by weight of methylaluminoxane having a cryoscopically determined molecular weight of 1300 g/mol) were introduced into the reactor and the mixture was stirred at 70° C. for 15 minutes. A solution of 2.5 mg of diphenylmethylene(9-fluorenyl)cyclopentadienyl)zirconium dichloride in 5 cm$^3$ of methylaluminoxane solution in toluene was added after 15 minutes preactivation.

Polymerization was carried out at 70° C. for one hour while stirring (750 rpm), with the ethylene pressure being maintained at 6.0 bar by metering in further amounts.

The reaction solution was drained into a vessel and quickly introduced into 5 dm$^3$ of acetone, the mixture was stirred for 10 minutes and the precipitated product was subsequently filtered off. The filter cake was washed a number of times alternately with 10% strength hydrochloric acid and acetone. Finally the cake was washed to neutrality and stirred with acetone. The polymer thus washed is filtered off and dried at 80° C. and a pressure of 0.2 bar for 15 hours.

31 g of a colorless polymer were obtained. A viscosity number VN of 122 cm$^3$/g and a glass transition temperature Tg of 156° C. were measured on the polymer.

Example 7: (Bulk Polymerization)

A dry 1.5 dm³ polymerization reactor fitted with stirrer was flushed with nitrogen and then with ethylene and was charged with 560 g of norbornene melt at 70° C. While stirring, the reactor was then maintained at a temperature of 70° C. and pressurized with 6 bar of ethylene (gage pressure).

5 cm³ of methylaluminoxane solution in toluene (10.1% by weight of methylaluminoxane having a cryoscopically determined molecular weight of 1300 g/mol) were then metered into the reactor and the mixture stirred at 70° C. for 15 minutes, with the ethylene pressure being maintained at 6 bar by metering in further amounts. In parallel thereto, 0.1 mg of dimethylsilyl(9-(2,7-di-tert-butyl)fluorenyl) cyclopentadienylzirconium dichloride were dissolved in 5 cm³ of methylaluminoxane solution in toluene and preactivated by allowing to stand for 15 minutes. The solution of the complex was then metered into the reactor. Polymerization was then carried out at 70° C. for 1 hour while stirring (750 rpm), with the ethylene pressure being maintained at 6 bar by metering in further amounts. The reaction solution was then drained into a vessel and quickly introduced into 5 dm³ of acetone, the mixture was stirred for 10 minutes and subsequently filtered.

The solid obtained was washed a number of times alternately with 10% strength hydrochloric acid and acetone, subsequently washed to neutrality and again stirred with acetone. The polymer was again filtered off and dried at 80° C. and a pressure of 0.2 bar for 15 hours.

15 g of a colorless polymer were obtained. A viscosity number VN of 271 cm³/g and a glass transition temperature Tg of 149° C. were measured.

Example 8 (Comparative Example to Example 7)

The polymerizations were carried out as in Example 7, with another catalyst being used (Table 1).

cm³ of $O_2$-free and $H_2O$-free toluene and 5 cm³ of $O_2$-free and $H_2O$-free $Et_2O$ under argon at room temperature and the mixture was stirred for a further 2 hours at room temperature. Subsequently the lithium salt was added dropwise at room temperature to a solution of 19.5 ml (162 mmol) of dichlorodimethylsilane in 35 ml of $O_2$-free and $H_2O$-free toluene and the mixture was stirred for a further 15 hours. Subsequently the precipitated lithium chloride was filtered off and the solvent was removed in vacuo. The residue was recrystallized from 50 ml of hot hexane. After filtration and washing with cold hexane, 12.4 g (62%) of product were obtained as colorless crystals.

The $^1$H-NMR (measured in $CDCl_3$) has the following signals (in ppm): 7.3–7.5 (m, 6H, arom. H), 4.0 (s, 1H, Flu-H), 1.4 (s, 18H, t-Bu-$CH_3$), 0.1 (s, 6H, Si-$CH_3$).

3. Dimethyl(2,7-di-tert-butylfluorenyl) cyclopentadienylsilane (3)

8.5 ml (21 mmol) of a 2.5M solution of butyllithium in hexane were added dropwise to 1.4 g (21 mmol) of cyclopentadiene in 45 ml of $O_2$-free and $H_2O$-free THF at 0° C. under argon and the mixture was stirred for a further 2 hours at room temperature. This solution was subsequently added at room temperature to a solution of 7.9 g (21 mmol) of 2 in 100 ml of $O_2$-free and $H_2O$-free THF over a period of 2 hours and the mixture was stirred for a further 1 hour at room temperature. 50 ml of $H_2O$ were added, the phases were separated and the aqueous phase was further extracted twice with 30 ml of $Et_2O$ each time. The combined organic phases were dried ($MgSO_4$) and the solvent was removed in vacuo. After chromatography on 200 g of silica gel (hexane/methylene chloride 20:1), 4.4 g (51%) of 3 were obtained as a colorless oil.

The $^1$H-NMR (measured in $CDCl_3$) has the following signals (in ppm): 7.3–7.8 (m, 6H, arom. H), 6.0–6.7 (m, 3H, Cp-H), 3.9 (s, 1H, Flu-H), 3.1 and 2.9 (m, 2H, Cp-H), 1.4 (s, 18H, t-Bu-$CH_3$), –0.1 and –0.3 (d, 6H, Si-$CH_3$).

4. Dimethylsilanediyl(2,7-di-tert-butylfluorenyl) cyclopentadienylzirconium dichloride (4)

TABLE 1

| Polymerization at specified temperature and pressure, reaction duration 1 hour | | | | | | | |
|---|---|---|---|---|---|---|---|
| Example No. | Metallocene (Mc) | Temp. (°C.) | Pressure (bar) | Mass of Mc (mg) | Yield (g) | VN (cm³/g) | $T_g$ (°C.) Method (toluene) |
| 1 | A | 70 | 6 | 0.1 | 13 | 259 | 142 85% strength solution |
| 2 | C | 70 | 6 | 0.2 | 11 | 197 | 126 85% strength solution |
| 3 | D | 70 | 6 | 0.3 | 39 | 169 | 160 85% strength solution |
| 4 | A | 40 | 6 | 0.5 | 20 | 405 | 125 85% strength solution |
| 5 | A | 40 | 1 | 0.7 | 6 | 370 | 186 85% strength solution |
| 6 | B | 70 | 6 | 2.5 | 31 | 122 | 156 85% strength solution |
| 7 | A | 70 | 6 | 0.1 | 15 | 271 | 149 Bulk |
| 8 | B | 70 | 6 | 3.0 | 33 | 140 | 159 Bulk |

A = dimethylsilyl (9-(2,7-di-tert-butyl)fluorenyl)cyclopentadienylzirconium dichloride
B = diphenylmethylene (9-fluorenyl)cyclopentadienylzirconium dichloride
C = dimethylsilyl (9-fluorenyl)cyclopentadienylzirconium dichloride
D = methylphenylsilyl (9-fluorenyl)cyclopentadienylzirconium dichloride
Mc = metallocene

Example 9

Dimethylsilanediyl(2,7-di-tert-butylfluorenyl) cyclopentadienylzirconium dichloride 1. 2,7-Di-tert-butylfluorenyl (1)

The preparation of 1 is carried out as in: Synthesis, 1984, 335, to which explicit reference is made here.

2. Dimethyl(2,7-di-tert-butylfluorenyl)chlorosilane (2)

21.6 ml (54 mmol) of a 2.5M solution of butyllithium in hexane were added dropwise to 15 g (54 mmol) of 1 in 80

10 ml (25 mmol) of a 2.5M solution of butyllithium in hexane were added at room temperature to 6.4 g (10.9 mmol) of 4 in 50 ml of $O_2$-free and $H_2O$-free $Et_2O$ under argon and the mixture was stirred for a further 18 hours at room temperature. The solvent was removed in vacuo, the residue was washed a number of times with hexane and subsequently dried for 2 hours at 0.1 torr and 40° C. The dilithio salt was suspended in 30 ml of $O_2$-free and $H_2O$-free toluene and admixed at –30° C. with 2.56 g (11 mmol) of $ZrCl_4$. The mixture was stirred further after 2 hours at room temperature and subsequently filtered through a G3 frit. The filtrate was admixed with hexane until turbid and allowed to crystallize at −35° C. 0.49 g (12%) of 4 was obtained as yellow-orange crystals.

The $^1$H-NMR (measured in CDCl$_3$) has the following signals (in ppm): 7.4–8.1 (m, 6H, arom. H), 6.6 and 5.6 (m, each 2H, Cp-H), 1.3 (s, 18H, t-Bu-CH$_3$), 1.1 (s, 6H, Si-CH$_3$).

The mass spectroscopically determined molecular weight is 560 g/mol.

What is claimed is:

1. A process for preparing a cycloolefin homopolymer or copolymer by polymerization of from 0.1 to 100% by weight, based on the total amount of monomers, of at least one polycyclic olefin of the formulae I, II, III, IV, V or VI

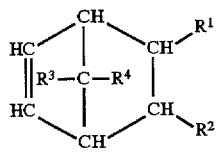
(I)

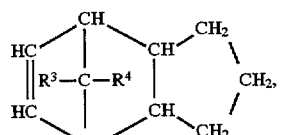
(II)

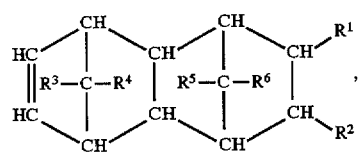
(III)

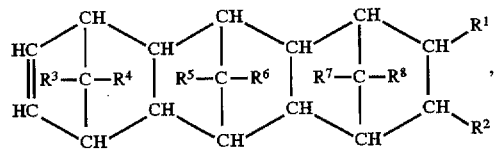
(IV)

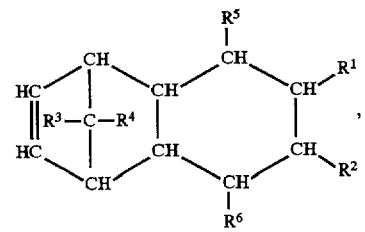
(V)

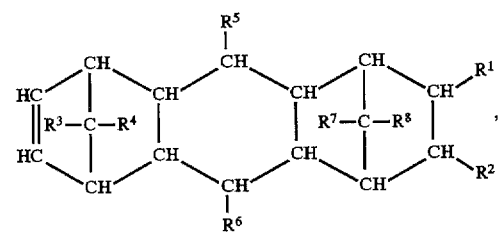
(VI)

in which $R^1$, $R^2$, $R^3$, $R^4$, $R^5$, $R^6$, $R^7$ and $R^8$ are identical or different and are a hydrogen atom or a $C_6$–$C_{10}$-aryl radical or a $C_1$–$C_8$-alkyl radical, with the same radicals in the various formulae being able to have a different meaning, from 0 to 99.9% by weight, based on the total amount of monomers, of a cycloolefin of the formula VII

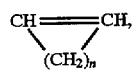
(VII)

in which n is a number from 2 to 10, and from 0 to 99.9% by weight, based on the total amount of monomers, of at least one acyclic 1-olefin of the formula VIII

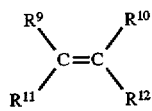
(VIII)

in which $R^9$, $R^{10}$, $R^{11}$ and $R^{12}$ are identical or different and are a hydrogen atom or a $C_6$–$C_{10}$-aryl radical or $C_1$–$C_8$-alkyl radical, at temperatures from 20° to 150° C. and a pressure from 0.01 to 64 bar, in the presence of a catalyst which comprises an aluminoxane of the formula IX

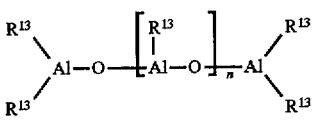
(IX)

for the linear type and/or of the formula X

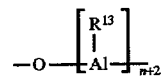
(X)

for the cyclic type, with, in the formulae IX and X, $R^{13}$ being a $C_1$–$C_6$-alkyl group or phenyl or benzyl and n being an integer from 2 to 50, and a metallocene of the formula

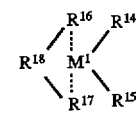
(XI)

in which $M^1$ is titanium, zirconium or hafnium, $R^{14}$ and $R^{15}$ are identical or different and are a hydrogen atom, a halogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group or a $C_8$–$C_{40}$-arylalkenyl group, $R^{16}$ is a substituted fluorenyl group, bearing one or more radicals which are identical or different and are a $C_1$–$C_{10}$ alkyl group, $C_1$–$C_{10}$-fluoroalkyl group, a $C_6$–$C_{10}$-fluoroaryl group, a $C_6$–$C_{10}$-aryl group, a $C_6$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkyl-aryl group, and $R^{17}$ is a cyclopentadienyl group, wherein $R^{18}$ is

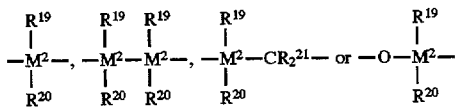

in which $M^2$ is silicon and $R^{19}$, $R^{20}$ and $R^{21}$ are identical or different and are a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{19}$ and $R^{20}$ or $R^{19}$ and $R^{21}$ in each case form a ring with the atoms connecting them.

2. The process as claimed in claim 1, wherein the polymerization is carried out in the liquid cycloolefin itself or in cycloolefin solution.

3. The process as claimed in claim 1, wherein the polycyclic olefin is norbornene or tetracyclododecene.

4. The process as claimed in claim 1, wherein a copolymer of norbornene and ethylene is prepared.

5. The process as claimed in claim 1, wherein at least one polycyclic olefin is of the formulas I or III, in which $R^1$, $R^2$, $R^3$, $R^4$, $R^5$, $R^6$, $R^7$ and $R^8$ are identical or different and are a hydrogen atom, a $C_6$–$C_{10}$-aryl radical or a $C_1$–$C_8$-alkyl radical where the same radicals can have different meaning in the various formulas.

6. The process as claimed in claim 5, wherein $R^9$, $R^{10}$, $R^{11}$ and $R^{12}$ are identical or different and are a hydrogen atom or $C_1$–$C_8$-alkyl group.

7. The process as claimed in claim 6, wherein $R^9$, $R^{10}$, $R^{11}$ and $R^{12}$ are identical or different and are ethylene or propylene.

8. The process as claimed in claim 1, wherein the temperature is from 20° to 150° C., n is an integer from 5 to 40, and wherein in the formulas IX and X, the radical $R^{13}$ is identical or different and is methyl, ethyl, isobutyl, butyl, neopentyl, phenyl or benzyl and n is an integer from 5 to 40, and the metallocene is dimethylsilandiyl(9-(2,7-di-tert.butyl)fluorenyl)cyclopentadienylzirconium dichloride.

9. The process as claimed in claim 5, wherein the metallocene of formula XI is dimethylsilandiyl(9-2,7-di-tert.butyl)fluorenyl)cyclopentadienylzirconium dichloride.

10. The process as claimed in claim 1, wherein the cycloolefin of formula VII is a substituted or unsubstituted cyclopentene.

11. A metallocene compound of the formula XI

(XI)

in which $M^1$ is titanium, zirconium or hafnium $R^{14}$ and $R^{15}$ are identical or different and are a hydrogen atom, a halogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group or a $C_8$–$C_{40}$-arylalkenyl group, $R^{16}$ is a fluoroenyl group bearing one or more radicals which are identical or different and are a $C_1$–$C_{10}$ alkyl group, $C_1$–$C_{10}$-fluoroalkyl group, a $C_6$–$C_{10}$-fluoroaryl group, a $C_6$–$C_{10}$-aryl group, a $C_6$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkyl-aryl group, and $R^{17}$ is a cyclopentadienyl group, wherein $R^{18}$ is

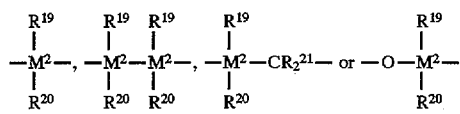

in which $M^2$ is silicon and $R^{19}$, $R^{20}$ and $R^{21}$ are identical or different and are a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{19}$ and $R^{20}$ or $R^{19}$ and $R^{21}$ in each case form a ring with the atoms connecting them.

12. The metallocene compound as claimed in claim 11, wherein $M^1$ is zirconium or hafnium.

13. The metallocene compound as claimed in claim 11, wherein $R^{14}$ and $R^{15}$ are identical or different and are a hydrogen atom, a $C_1$–$C_3$-alkyl group, a $C_1$–$C_3$-alkoxy group, a $C_6$–$C_8$-aryl group, a $C_6$–$C_8$-aryloxy group, a $C_2$–$C_4$-alkenyl group, a $C_7$–$C_{10}$-arylalkyl group, a $C_7$–$C_{12}$-alkylaryl group, a $C_8$–$C_{12}$-arylalkenyl group or a chlorine atom.

14. The metallocene as claimed in claim 13, wherein $M^1$ is zirconium.

15. The metallocene as claimed in claim 11, wherein $R^{18}$ is

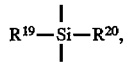

16. The metallocene as claimed in claim 15, wherein $R^{18}$ is

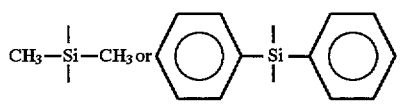

17. The metallocene as claimed in claim 11, wherein the metallocene is dimethylsilandiyl(9-(2,7-di-tert butyl)fluorenyl)cyclopentadienylzirconium dichloride.

* * * * *